US008821580B2

(12) United States Patent
DaSilva

(10) Patent No.: US 8,821,580 B2
(45) Date of Patent: Sep. 2, 2014

(54) SYSTEM FOR MAKING A BONE REPAIR

(75) Inventor: Manuel DaSilva, East Greenwich, RI (US)

(73) Assignee: Swiss Ortho, LLC, East Greenwich, RI (US)

( * ) Notice: Subject to any disclaimer, the term of this patent is extended or adjusted under 35 U.S.C. 154(b) by 980 days.

(21) Appl. No.: 12/209,226

(22) Filed: Sep. 12, 2008

(65) Prior Publication Data

US 2009/0312802 A1 Dec. 17, 2009

Related U.S. Application Data

(60) Provisional application No. 60/972,029, filed on Sep. 13, 2007.

(51) Int. Cl.
*A61F 2/42* (2006.01)
*A61B 17/80* (2006.01)
*A61B 17/68* (2006.01)
*A61B 17/17* (2006.01)

(52) U.S. Cl.
CPC ........... *A61B 17/683* (2013.01); *A61B 17/8061* (2013.01); *A61B 2017/1782* (2013.01); *A61B 17/1728* (2013.01)
USPC ........................... 623/21.11; 606/71; 606/297

(58) Field of Classification Search
CPC .............. A61B 17/80; A61B 17/8057; A61B 17/8061; A61F 2002/4261; A61F 2002/4264–2002/4297; A61F 5/05858; A61F 5/05866; A61F 2007/0035; A61F 13/107
USPC ................... 606/902, 906, 604, 71, 284, 297; 623/18.11, 21.11–21.15
See application file for complete search history.

(56) References Cited

U.S. PATENT DOCUMENTS

| | | | |
|---|---|---|---|
| 2,825,329 A | 3/1958 | Caesar | |
| 3,709,218 A | 1/1973 | Halloran | |
| 3,900,025 A * | 8/1975 | Barnes, Jr. | 606/71 |
| 4,360,012 A * | 11/1982 | McHarrie et al. | 606/54 |
| 4,794,918 A | 1/1989 | Wolter | |
| 4,969,886 A * | 11/1990 | Cziffer et al. | 606/59 |
| 5,006,120 A | 4/1991 | Carter | |
| 5,197,966 A | 3/1993 | Sommerkamp | |
| 5,529,075 A * | 6/1996 | Clark | 128/898 |
| 5,722,976 A * | 3/1998 | Brown | 606/281 |
| 5,935,128 A | 8/1999 | Carter et al. | |
| 6,129,730 A * | 10/2000 | Bono et al. | 606/71 |
| 6,623,486 B1 * | 9/2003 | Weaver et al. | 606/281 |
| 7,090,676 B2 | 8/2006 | Huebner et al. | |
| 7,153,309 B2 | 12/2006 | Huebner et al. | |
| 7,294,130 B2 | 11/2007 | Orbay | |
| 2002/0032446 A1 | 3/2002 | Orbay | |

(Continued)

*Primary Examiner* — Christopher D Prone
(74) *Attorney, Agent, or Firm* — Knobbe Martens Olson & Bear LLP

(57) ABSTRACT

A method and system is provided for repairing bone fractures at locations where high levels of stability are required. The system employs two plates to buttress a fracture from both the dorsal and volar sides. The plates are affixed to one another using screws that are installed from a volar plate, through the bone and into a dorsal plate. The method provides for use of a directional guide that allows the precise placement of Kirschner wires for temporary fixation of the fracture, installation of a first bone fixation plate using the installed K-wires for alignment, installation of a second bone plate adjacent the bone to be repaired and opposite the first bone plate, and installation of cannulated fasteners between the two opposing bone plates such that the fasteners rigidly engage both of the bone plates.

7 Claims, 5 Drawing Sheets

(56) References Cited

U.S. PATENT DOCUMENTS

| | | |
|---|---|---|
| 2002/0156474 A1 | 10/2002 | Wack et al. |
| 2003/0153918 A1 | 8/2003 | Putnam et al. |
| 2004/0059335 A1 | 3/2004 | Weaver et al. |
| 2004/0172029 A1* | 9/2004 | Lerch .............................. 606/71 |
| 2005/0085818 A1 | 4/2005 | Huebner |
| 2005/0085819 A1 | 4/2005 | Ellis et al. |
| 2005/0234472 A1 | 10/2005 | Huebner |
| 2006/0264949 A1* | 11/2006 | Kohut et al. ................... 606/69 |

* cited by examiner

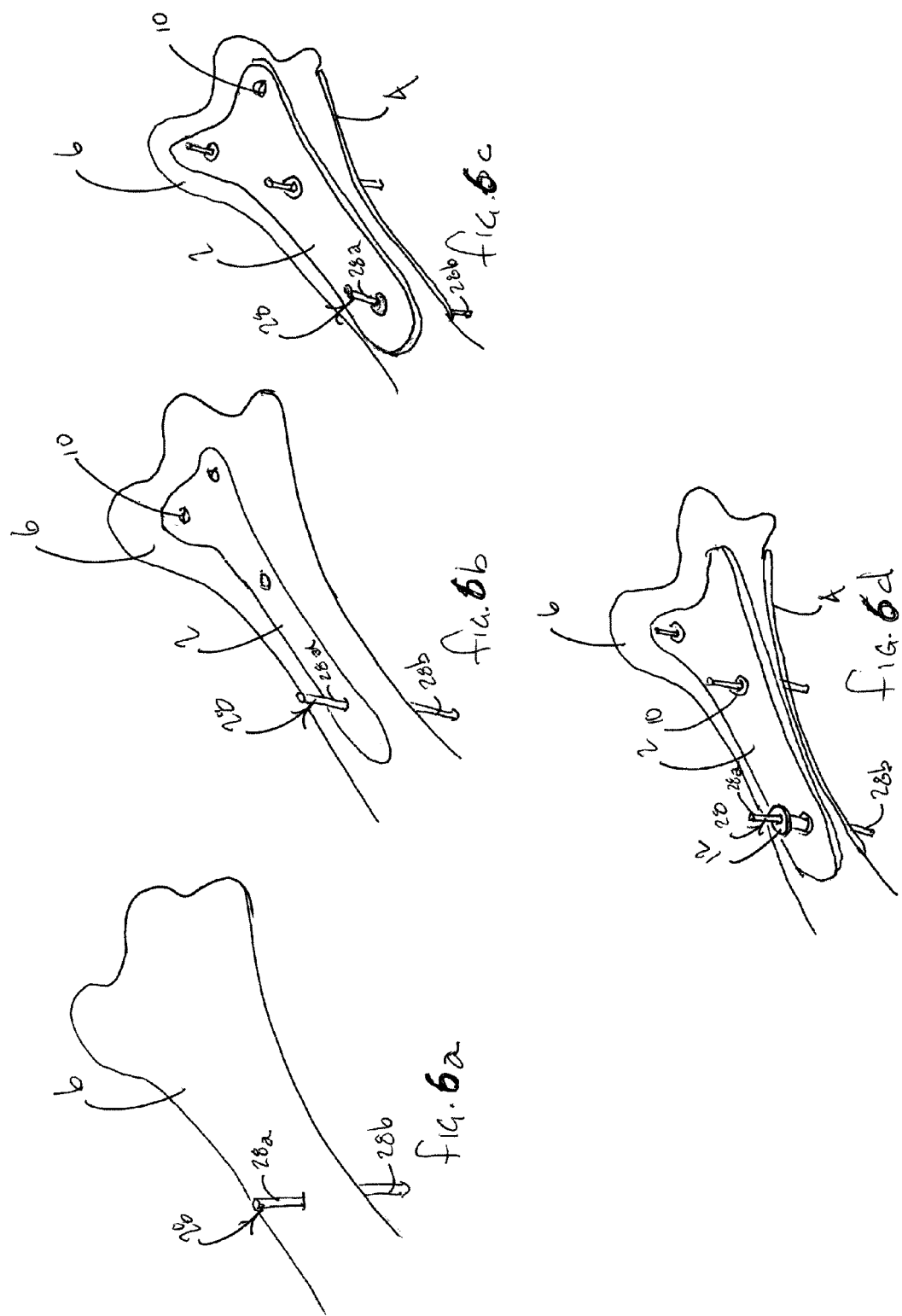

SYSTEM FOR MAKING A BONE REPAIR

CROSS-REFERENCE TO RELATED APPLICATIONS

This application is related to and claims priority from earlier filed U.S. Provisional Patent Application No. 60/972,029, filed Sep. 13, 2007.

BACKGROUND OF THE INVENTION

The present invention relates generally to a method and system for use in the positive and secure positioning of fractured bones. More specifically, the present invention relates to double plate assembly for use in repairing bone fractures that demonstrates improved stability when buttressing fractures that exhibit complex articular patterns and comminution.

The human skeleton consists of 206 individual bones that cooperate to perform a variety of important functions such as support, movement, protection, storage of minerals, and formation of blood cells. The bones within the skeleton are generally grouped into two categories, the axial skeleton and the appendicular skeleton. The axial skeleton includes 80 bones that make up the body's center of gravity and the appendicular skeleton includes the remaining 126 bones that make up the body's appendages.

When a person suffers a bone injury such as a bone fracture, it is important that the fractured bone be repaired promptly and properly. When such a fracture is severe enough, repair often requires remedies that may include surgical intervention. The typical treatment for a fractured bone involves the use of a fixation device that serves to reinforce the fractured bone and keep the adjacent portions of the bone aligned during healing. A wide variety of fixation devices are employed to maintain bone alignment. Further, these bone fixation devices take a variety of forms, including external devices such as casts and internal devices such as bone plates and screws. As can be appreciated by one skilled in the art, bone repairs employing external devices are minimally invasive, allowing reduction and fixation of simple fractures from outside the body. In contrast, bone plates are internal devices that mount directly to bone to span and support the fracture and require a fairly invasive process for placement and installation thereof.

While most bones in the skeleton are susceptible to injury or fracture, the repair method used depends on the location of the bone and the proximity of the break to a joint. Further, some bones require a more precise repair as compared to others in order to insure stability of the joint. For example, the radius is one of two long bones found in the human forearm. Distal fractures of the radius are a common result of forward falls, with the palms facing downward, particularly among the elderly. In such falls, force exerted on the distal radius at impact frequently produces dorsal displacement of one or more bone fragments created distal to the fracture site. Unfortunately, internal fixation of such dorsally displaced bone fragments using bone plates has proved problematic. Using dorsal fixation, a surgeon may apply a reducing force on the fracture by attaching a bone plate to the dorsal side of the radius. However, unless the bone plate has a very low profile, dorsal tendons overlying the bone plate may rub against it, producing tendon irritation or even tendon rupture.

Alternatively, fixation may be performed volarly. In this approach, a surgeon may attach a bone plate to the volar side of the radius. The volar side of the radius may be more accessible surgically and defines a distal pocket in which the distal portion of the bone plate may be disposed. Accordingly, the bone plate may be less obtrusive and its placement at this location may produce less tendon irritation, even if the bone plate is thicker and sturdier. However, while volar fixation provides advantages as compared to dorsal fixation, there are settings where a single volar or dorsal implant does not provide enough stability to provide reliable support for the bony structures. This is particularly problematic in elderly patients that generally have poor quality bone or in high-speed injuries with highly comminuted fracture patterns. In these situations, bone screws used for fastening the plate in place are inserted through openings in the plate. The difficulty is that when the screws are installed into the distal radius, they may not find sufficient bone structure to hold distal bone fragments in position against the bone plate. In addition, it should be appreciated by one skilled in the art that this scenario is not unique to distal radius fractures. It also happens, for example, in distal humerus, proximal olecranon, distal ulna, proximal tibia and distal tibia (pilon) injuries when in certain situations it is necessary to use double plates in order to provide the best mechanical construct.

Therefore there is a need for an alternative strategy for reducing and fixing bone fractures that exhibit complex articular patterns and comminution. There is a further need for a method and system that retains the fractured portions of bone in a rigid structure that does not rely on fastening directly to the bone itself for reducing and fixing the bone fracture

BRIEF SUMMARY OF THE INVENTION

In this regard, the present invention provides a method and system for making a bone repair that is useful in repairing bone fractures at fracture locations where high levels of stability are required. Generally, the present invention is directed to a bone repair system that employs two plates to buttress a fracture from both the dorsal and volar sides and a method of employing the system to achieve an effective bone repair. The plates are affixed to one another using screws that are installed from a volar plate, through the bone and into a dorsal plate. The use of these complimentary dorsal and volar plates creates a highly stable repair structure while requiring fewer screws as compared to the prior art.

In one preferred embodiment of the present invention two bone plates are employed on opposing sides of the bone that has suffered a fracture that must be buttressed. Depending on the extent and severity of the fracture being buttressed, the method and system of the present invention may employ two full plates extending along opposing sides of the bone or a full plate on the volar side of the bone and at least one partial plate on the dorsal side. Generally, the object of the present invention is to provide a volar plate that spans and buttresses the fracture while providing at least one secondary dorsal plate that provides support into which the bone screw extending upwardly from the volar plate engages thereby eliminating the need to anchor the bone screw in the bone structure itself.

By installing the bone plates of the present invention, fixation of the bone fragments is achieved using screws that engage both the dorsal and volar plates in a manner that rigidly maintains the plates in position relative to one another and the bone to be repaired without requiring that the fasteners engage with the bone itself. This allows the method and system of the present invention to be particularly useful in applications where the fractures is particularly severe, exhibiting complex articular patterns and comminution and applications where the fasteners cannot be reliably fastened into the bone itself.

Additionally, the method provided in the present invention provides for the insertion of a first Kirschner wire (K-wire) for temporary reduction and fixation of the fracture. Installation of at least a first bone fixation plate using the installed K-wires for alignment. Installation of at least a second partial bone plate adjacent the bone to be repaired and opposite the first bone plate. Installation of fasteners that fasten the two opposing bone plates to one another such that the fasteners rigidly engage both of the bone plates.

It is therefore an object of the present invention to provide a method and system for reducing and fixing bone fractures that exhibit complex articular patterns and comminution. It is a further object of the present invention to provide a method and system that retains the fractured portions of bone in a rigid structure that does not rely on fastening directly to the bone itself for reducing and fixing the bone fracture.

These together with other objects of the invention, along with various features of novelty that characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In the drawings which illustrate the best mode presently contemplated for carrying out the present invention:

FIGS. 6a-6d are illustrations showing the method of the present invention.

DETAILED DESCRIPTION OF THE INVENTION

Figure 1:
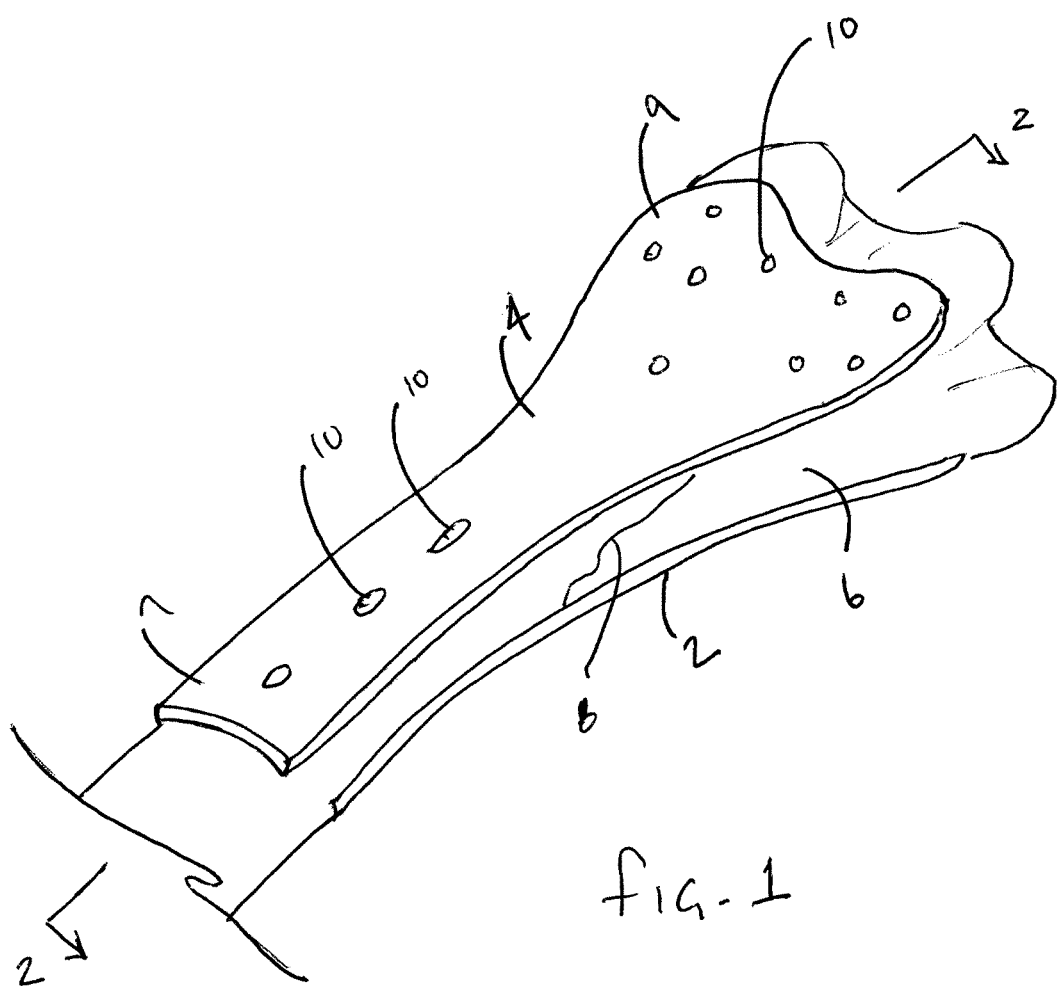
FIG. 1 is a perspective view of the system of the present invention installed about a bone.

Now referring to the drawings, the bone repair system of the present invention is shown and generally illustrated at FIGS. 1-5 while the method of the present invention is depicted at FIG. 6. Generally, the present invention is directed to a bone repair system that employs two complimentary opposing plates to buttress a fracture from both sides of a bone. In one example, in a repair involving a wrist fracture, the plates are affixed to one another using screws that are installed from a volar plate, through the bone and into the dorsal plate. The use of these complimentary volar and dorsal plates creates a highly stable repair structure while requiring fewer screws thereby minimizing the degree of soft tissue dissection.

Turning now to FIG. 1, in the preferred embodiment of the present invention two complimentary opposing bone plates 2, 4 are employed on opposing sides of the bone 6 having the fracture 8 to be buttressed. While the bone 6 to be repaired as depicted in FIG. 1 is the radius, one skilled in the art can appreciate that the method and system of the present invention is equally applicable to a number of bones throughout the body and accordingly, the teachings of this invention are not limited to the repair of the radius but are equally applicable to any fracture that requires a high stability repair. Generally, the object of the present invention is to provide a first plate 2 that spans and buttresses the fracture while providing at least one secondary plate 4 that provides support into which the bone screw extending upwardly from the volar plate engages, as will be described in detail below, thereby eliminating the need to anchor the bone screw in the bone 6 structure itself.

Figure 2:
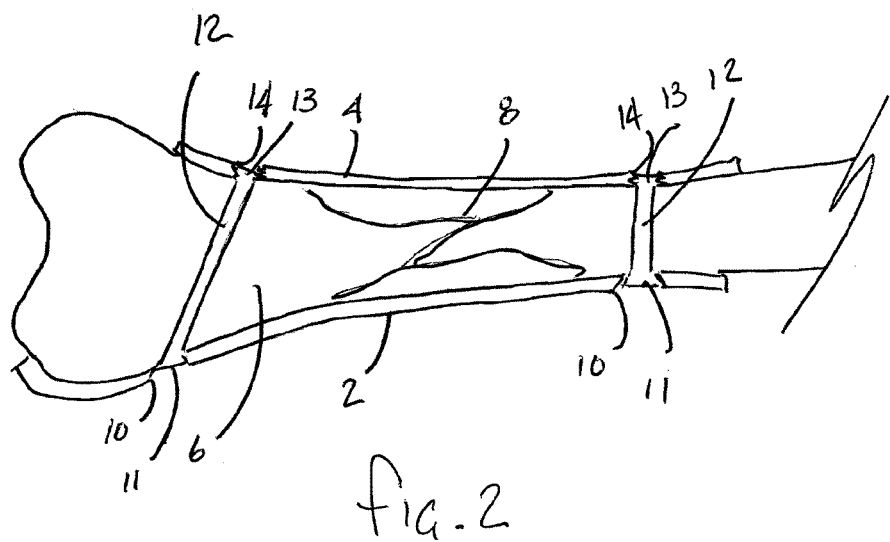
FIG. 2 is a cross-sectional view of the system of the present invention along line 2-2 of FIG. 1.

Turning now to the cross-sectional view depicted at FIG. 2 in connection with FIG. 1, it can be seen that the first plate 2 is preferably a full plate installed adjacent the volar side of the bone and includes holes 10 or more preferably slots therein that allow the placement of bone screws 12 therethrough. The holes 10 or slots are configured to allow the shank of the screw 12 to pass yet to engage the head of the screw 12 once the screw 12 is fully installed and tightened. The at least one secondary plate 4 positioned adjacent the dorsal side of the bone includes a hole 14 therein that is particularly configured to receive and engage the threads on the distal end 13 of the screw 12 opposite the head 11. Upon tightening of the screw 12, the screw 12 draws the secondary plate 14 against the fractured bone fragment 8 drawing the fractured bone fragment 8 against the first plate 2 and clamping the bone 6 between the two complimentary opposing plates 2,4.

The plates 2,4 and fasteners 12 may be formed from any medical grade material suitable for permanent placement within the human body including but not limited to titanium, stainless steel, and absorbable materials. Further, it should be appreciated by one skilled in the art that the inner surfaces of the first and second plates 2,4 may be provided with an inner surface that is contoured to fit the bone 6 held therebetween.

Figure 3:
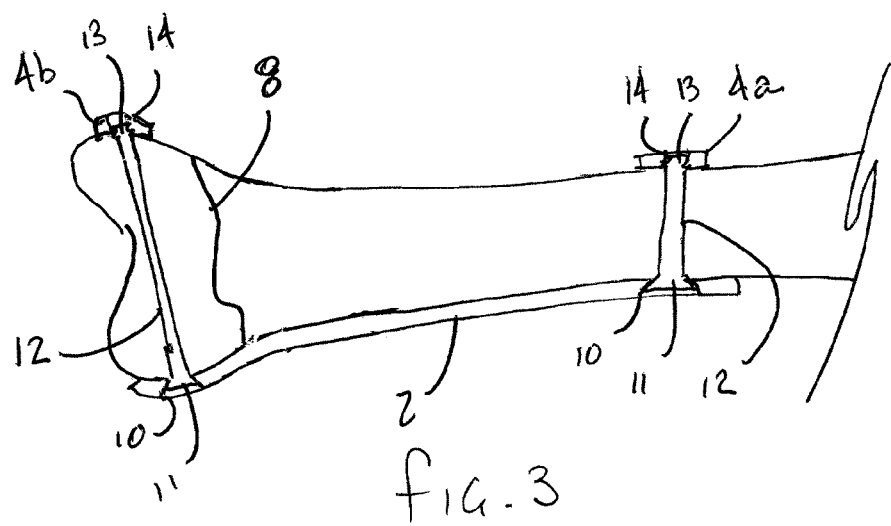
FIG. 3 is a cross-sectional view of the system of the present invention along line 2-2 of FIG. 1 depicting an alternate dorsal plate.

FIG. 3 depicts an alternate cross-sectional view wherein a second plate employed on the dorsal side is actually a pair of partial plates 4a,4b that are installed at the fastener 12 locations. In this regard, it should be appreciated that the present invention may also be implemented by installing a full plate 2 on the volar side and at least one partial plate 4a on the dorsal side or a plurality of partial plates 4a, 4b on the dorsal side.

In the most general sense therefore, referring back to FIGS. 1-3, the present invention provides a system for fixation of bone fractures that includes a first plate 2 having a proximal portion 7, a distal portion 9 and a plurality of apertures 10 formed therethrough, wherein the first plate 2 is configured to be received adjacent a first side of a fractured region 8 in a bone 6. At least one second plate member 4 is provided wherein the second plate 4 includes at least one aperture 10 formed therethrough, the second plate 4 being configured to be received adjacent a second opposing side of the fractured region 8 in a bone 6. Finally, a fastener 12 having a proximal end 11 and a distal end 13 is installed through the bone 6 to engage the first plate 2 and second plate 4 via the apertures 10 therein in order to lock the plates 2,4 relative to one another and provide stability and support to the fractured region 8.

Figure 4:
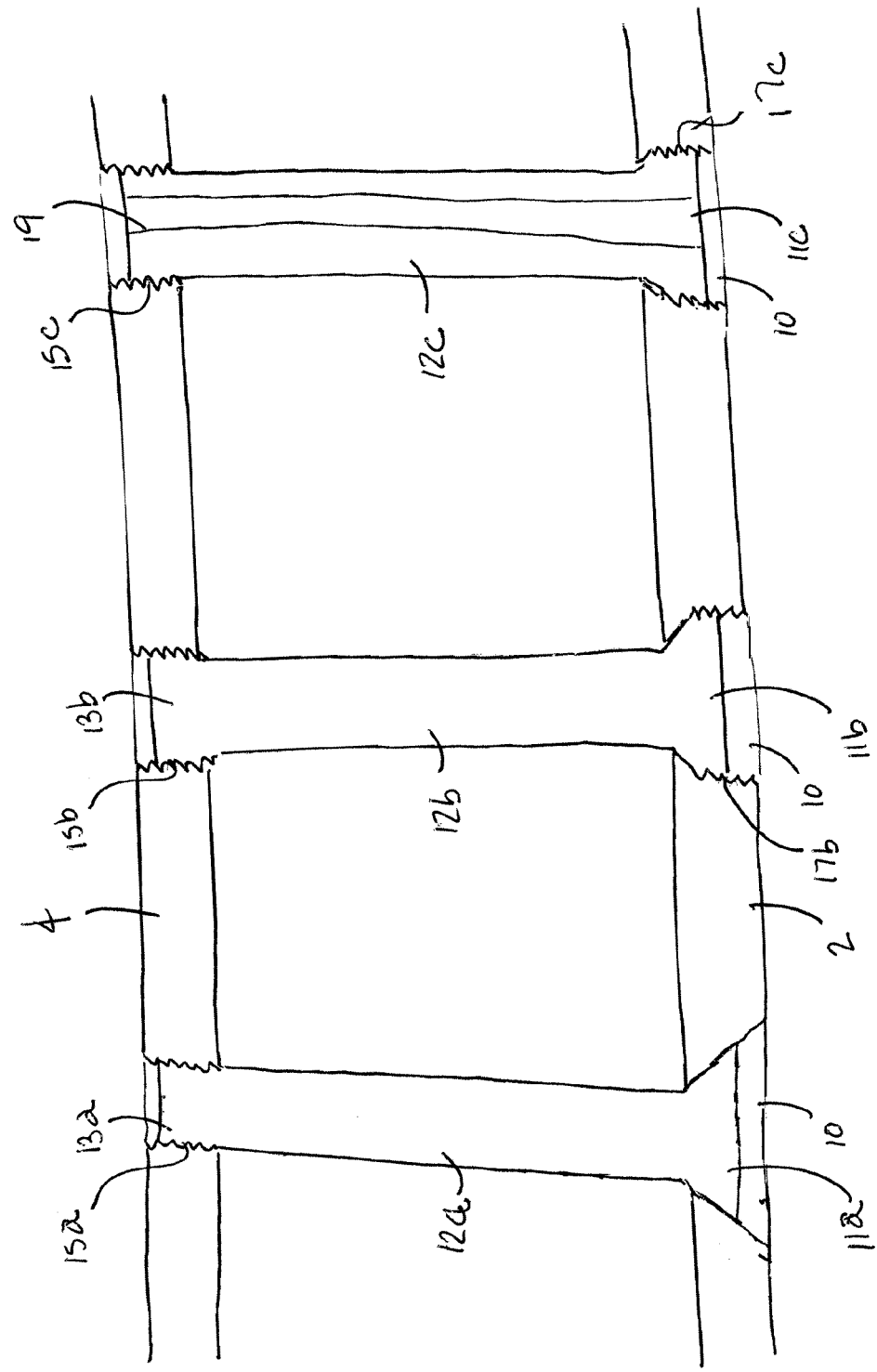
FIG. 4 is an illustration of various fasteners and locking aperture configurations that may be employed in the context of the present invention.

Turning now to FIG. 4, a plurality of fastener configurations 12a, 12b, 12c are depicted that is suitable for use in connection with the present invention. In the most general sense, as depicted in the first fastener 12a at the left of FIG. 4, the fastener 12 a is a screw that includes a head 11a that engages with the aperture 10 formed in the first plate 2 either using the tapered head or a pan head screw residing in a recess formed in the top surface of the first plate 2 so that the screw head 11a does not protrude over the top surface of the plate 2 resulting in irritation of the tissues surrounding the plate 2. At the distal end 13a of the faster 12a, threads are shown that engage with corresponding threads 15a in the aperture 10 formed in the second plate 4. Again, a fastener 12a is employed of the appropriate length such that the distal end 13a does not protrude through the surface of the second plate 4.

The second fastener 12b depicted at the center of FIG. 4 shows threads 15b, 17b on both the head at the proximal end 11b of the fastener 1 2b as well as distal end 13b of the fastener 12b wherein the threads 17b, 15b on the fastener 12b engage corresponding threads formed in the apertures 10 of the first plate 2 and second plate 4. This allows the plates 2, 4 to be engaged with one another and maintained in rigid spaced relation relative to one another despite the condition of the bone at the fractured region. It should be further appreciated that the threading shown and described herein is intended to be of a locking type such as known in the art wherein a differential in the thread pattern on the screw and the thread pattern in the aperture causes the screw to lock relative to the plates once installed and fully tightened. Such locking methods are well known in the art and therefore do not need to be more fully detailed herein.

Turning to the fastener 12c depicted at the left of FIG. 4, the faster 12c is shown to be cannulated. In other words, the fastener 12c includes a passage 19 therethrough that extends between the proximal 11c and distal ends 13c. Such a passageway 19 allows the screw 12c to be installed over a guide such as a Kirchner wire (K-wire) as will be described in more detail below. Further, the distal end 13c of the fastener 12c is preferably self-drilling to allow it to be installed directly through the bone in accordance with the method as detailed below.

Figure 5:
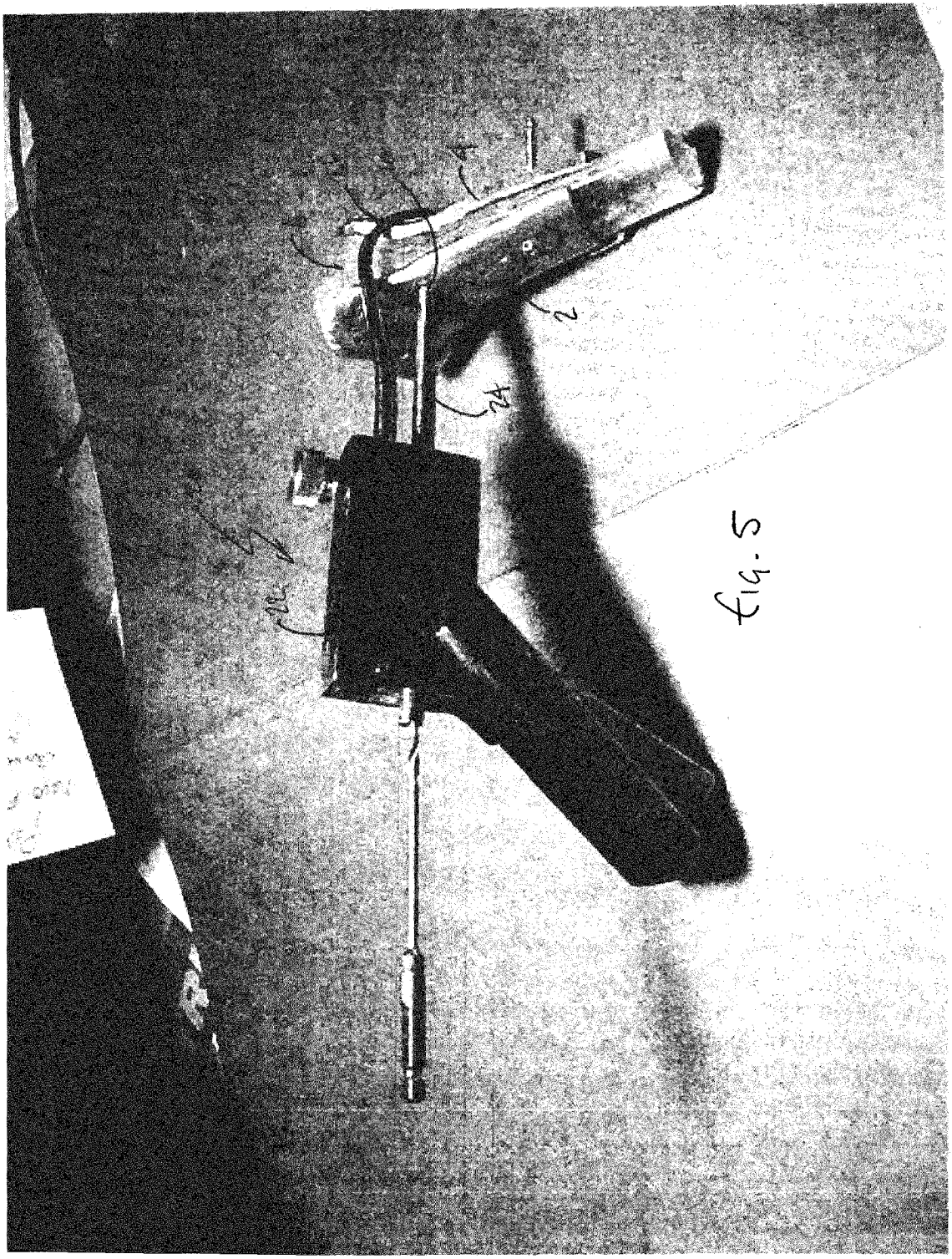
FIG. 5 is a guide device employed in the bone repair system of the present invention.

FIG. 5 shows a guide device 20 for use in connection with the bone repair system of the present invention. The guide device 20 has a body 22 that includes an alignment tube 24 extending therethrough. The guide tube 24 is positioned adjacent an aperture 10 in the first plate 2. In addition, the guide device 20 includes a secondary guide element 26 that extends thereform wherein the secondary guide element 26 is positioned in alignment with an aperture 10 in the second plate 4 on the opposite side of the bone 6. In this arrangement, the guide device 20 holds the first plate 2 and second plate 4 in compression relative to one another and the guide tube 24 is held in alignment such that the longitudinal axis of the guide tube 24 is precisely aligned through the apertures 10 in the first and second plates 2, 4.

In terms of a method for repairing a bone fracture, the present invention provides a method for fixation of bone fractures as depicted at FIGS. 6a-6d. In the most general embodiment of the method, a first plate 2 having a proximal portion, a distal portion and a plurality of apertures 10 formed therethrough is positioned adjacent a first side of a fractured region in a bone 6, at least one second plate 4 member having at least one aperture 10 formed therethrough is then positioned adjacent a second opposing side of said fractured region in a bone 6. With the plates 2, 4 positioned, the first plate 2 and second plate 4 are secured to one another using at least one fastener 12 having a proximal end and a distal end that engages between one of the apertures 10 in the first plate 2, through the bone 6 and into one of the apertures 10 in the second plate 4.

More preferably the method includes a step as shown at FIG. 6a wherein a Kirschner wire 28 is installed through the bone. Preferably this installation is accomplished using a guide 20 such as is depicted at FIG. 5 to precisely align and install the K-wire 28 into the bone. The K-wire 28, upon installation includes a first end 28a extending from one side of the bone 6 and a second end 28b extending from an opposing side of the bone 6. Once the K-wire 28 is installed, the first plate 2 is positioned by aligning one of the plurality of apertures 10 therein about the first end 28a of the Kirschner wire 28 (see FIG. 6b). Subsequently, the at least one second plate 4 is positioned about the second end 28b of the Kirschner wire 28 (see FIG. 6c). Finally, a cannulated fastener 12 is installed directly over the K-wire 28 such that the fastener 12 is self-drilling and is guided into place about the K-wire 28 (see FIG. 6d). The fastener 12 then engages the first plate 2 and second plate 4 as described above.

Alternately, the steps of the method may proceed by first installing a guide device 20 in alignment with a first aperture 10 in the first plate 2 adjacent a first side of the bone 6 such that the guide device 20 secondary guide element 26 is in alignment with a second position on an opposing side of the bone 6. The guide device 20 is then used to install a Kirschner wire 28 having a first end 28a extending from the first aperture 10 and a second end 28b extending from said second position on the opposing side of the bone 6. Next, at least one second plate 4 is positioned by aligning at least one aperture 10 therein about the second end 28b of the Kirschner wire 28. Finally, the first plate 2 is secured to the at least one second plate 4 by installing at least one fastener 12 having a proximal end and a distal end and a cannulated passage extending therebetween, wherein the cannulated passage is installed over the Kirschner wire 28, such that the fastener 12 installation is directed by the Kirschner wire 28 between the first aperture 10 in the first plate 2, through the bone 6 and into engagement with the at least one aperture 10 in the second plate 4. Further, the above process may be accomplished by first positioning the first plate 2 and second plate 4 and aligning the guide device 20 using the apertures 10 therein.

Such a system as disclosed within the present invention provides for the application of high rigidity buttressing to fractures without requiring that the screw anchor into the bone fragments themselves. As a result, fewer screws are required to secure fractures exhibiting comminution and higher stability is achieved.

It can therefore be seen that the present invention provides a system and method that facilitates the application of high rigidity buttressing to fractures without requiring that the screw anchor into the bone fragments themselves. As a result, fewer screws are required to secure fractures exhibiting comminution and higher stability is achieved. For these reasons, the instant invention is believed to represent a significant advancement in the art, which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. A bone fracture buttressing system for stable fixation of complex bone fractures, the system comprising:
   a first volar plate having an outer surface, an inner surface, and a first plurality of apertures formed therethrough, the first plurality of apertures comprising threads, the first volar plate configured to be received internal to a patient, the inner surface contoured to substantially conform to and be in direct contact with a first side of a fractured region of a volar side of a radius bone, the inner surface sized to span the first side of the fractured region;
   a second dorsal plate having an outer surface, an inner surface, and a second plurality of apertures formed therethrough, the second plurality of apertures comprising threads, the second dorsal plate configured to be received internal to the patient, the inner surface of the second dorsal plate contoured to substantially conform to and be in direct contact with a second side of the fractured region of a dorsal side of the radius bone, the second side being opposite the first side, the second dorsal plate being smaller than the first volar plate; and a plurality of fasteners each having a proximal end and a distal end, the distal end comprising threads and a first length, the distal end threads configured to lock in place within one of the second plurality of apertures and the first length sized to enable the distal end to not protrude beyond the outer surface of the second dorsal plate when the distal end threads are locked in place, the proximal end comprising a threaded head configured to lock in place within one of the first plurality of apertures, the head comprising a second length, the second length sized to enable the head to not protrude beyond the outer surface of the first volar plate when the head is locked in place, the plurality of fasteners extending through the radius bone and at least one of the plurality of fasteners is positioned substantially parallel to a joint surface of the radius bone, the plurality of fasteners are positioned in locked engagement with the first volar plate and the second dorsal plate to maintain the first volar plate and second dorsal plate in a rigid spaced relation, the plurality of fasteners having a non-threaded center portion extending between the distal end threads and the threaded head at the proximal end, the plurality of fasteners configured to extend from the first volar plate to the second dorsal plate.

2. The system of claim 1, wherein the threads of the first plurality of apertures are locking threads configured to engage the threaded head of the proximal end of the plurality of fasteners.

3. The system of claim 1, wherein the threads of the second plurality of apertures are locking threads configured to engage the threads of the distal end of the plurality of fasteners.

4. The system of claim 1, wherein the plurality of fasteners are cannulated.

5. The system of claim 1, wherein the plurality of fasteners are self-drilling.

6. The system of claim 1, wherein the second dorsal plate comprises a plurality of second dorsal plates.

7. The system of claim 1, wherein the second dorsal plate comprises an additional dorsal plate configured to be secured adjacent a dorsal surface region of the radius bone.

* * * * *

UNITED STATES PATENT AND TRADEMARK OFFICE
CERTIFICATE OF CORRECTION

PATENT NO.         : 8,821,580 B2
APPLICATION NO.    : 12/209226
DATED              : September 2, 2014
INVENTOR(S)        : Manuel DaSilva It is certified that error appears in the above-identified patent and that said Letters Patent is hereby corrected as shown below:

In the Specification

In column 2 line 28, Change "fracture" to --fracture.--.

In column 5 line 6, Change "1 2b" to --12b--.

In column 5 line 36, Change "thereform" to --therefrom--.

Signed and Sealed this
Twenty-eighth Day of April, 2015

Michelle K. Lee
*Director of the United States Patent and Trademark Office*